United States Patent
Leinsing

[11] Patent Number: 6,142,446
[45] Date of Patent: Nov. 7, 2000

[54] MEDICAL ADAPTER HAVING NEEDLELESS VALVE AND SHARPENED CANNULA

[75] Inventor: Karl R. Leinsing, Raleigh, N.C.

[73] Assignee: Alaris Medical Systems, Inc., San Diego, Calif.

[21] Appl. No.: 09/197,017

[22] Filed: Nov. 20, 1998

Related U.S. Application Data

[63] Continuation of application No. 08/794,404, Feb. 2, 1997, Pat. No. 5,839,715, which is a continuation-in-part of application No. 08/705,062, Aug. 29, 1996, Pat. No. 5,676,346, which is a continuation of application No. 08/442,025, May 16, 1995, abandoned.

[51] Int. Cl.⁷ .................................................. F16K 51/00
[52] U.S. Cl. ................................... 251/149.1; 251/149.6; 604/256; 604/905
[58] Field of Search ........................... 251/149.1, 149.6; 604/256, 905

[56] References Cited

U.S. PATENT DOCUMENTS

| | | | |
|---|---|---|---|
| Re. 35,841 | 7/1998 | Frank et al. | 604/256 |
| 4,425,122 | 1/1984 | Cohen | 604/237 |
| 4,874,377 | 10/1989 | Newgard et al. | 604/167 |
| 4,981,469 | 1/1991 | Whitehouse et al. | 604/86 |
| 5,064,416 | 11/1991 | Newgard et al. | 604/167 |
| 5,120,324 | 6/1992 | Sancoff | 604/283 |
| 5,122,123 | 6/1992 | Vaillancourt | 604/192 |
| 5,188,620 | 2/1993 | Jepson et al. | 604/283 |
| 5,251,873 | 10/1993 | Atkinson et al. | 251/149.1 |
| 5,295,658 | 3/1994 | Atkinson et al. | 251/149.1 |
| 5,330,450 | 7/1994 | Lopez | 604/283 |
| 5,338,313 | 8/1994 | Molenauer et al. | 604/229 |
| 5,344,414 | 9/1994 | Lopez et al. | 604/283 |
| 5,402,982 | 4/1995 | Atkinson et al. | 251/149 |
| 5,470,319 | 11/1995 | Mayer | 604/167 |
| 5,509,433 | 4/1996 | Paradis | 137/1 |
| 5,616,129 | 4/1997 | Mayer | 604/167 |
| 5,616,130 | 4/1997 | Mayer | 604/167 |
| 5,699,821 | 12/1997 | Paradis | 137/1 |
| 5,806,831 | 9/1998 | Paradis | 251/149.1 |
| 5,820,601 | 10/1998 | Mayer | 604/167 |

FOREIGN PATENT DOCUMENTS

| | | | |
|---|---|---|---|
| 0 309 771 A1 | 9/1988 | European Pat. Off. | A61M 5/00 |
| 0 453 264 A1 | 4/1991 | European Pat. Off. | |
| 0453265 | 10/1991 | European Pat. Off. | |
| 0 497 229 A1 | 1/1992 | European Pat. Off. | |
| 3303718 C1 | 4/1984 | Germany | A61M 5/14 |
| WO 93/20772 | 10/1993 | WIPO | |
| WO 9528195 | 10/1995 | WIPO | |

*Primary Examiner*—A. Michael Chambers
*Attorney, Agent, or Firm*—Fulwider, Patton Lee & Utecht, LLP

[57] ABSTRACT

A medical adapter having both a needleless valve and a sharpened cannula is used to connect or adapt pierceable septa containers or other devices having different sizes to needleless connection. The adapter includes a needleless site at one end and a sharpened cannula at the other end protected by spring arms. These arms include claws at their distal ends to grasp the neck of the pierceable septum device to which the sharpened cannula is to be inserted. The claws include sharpened points for gripping the device. The arms are located on either side of the adapter body and are connected to the body through springs. Handles are also included on the arms for use by the operator to separate the arms against the spring forces during engagement of the adapter with the septum. In one case, the handles include finger grips located above the springs for pressing the handles inward to open the arms and claws and in another case, the handles are located closer to the distal ends of the arms for pulling the arms outward. The adapter in one case comprises only three parts for reduced materials and manufacturing expense.

20 Claims, 12 Drawing Sheets

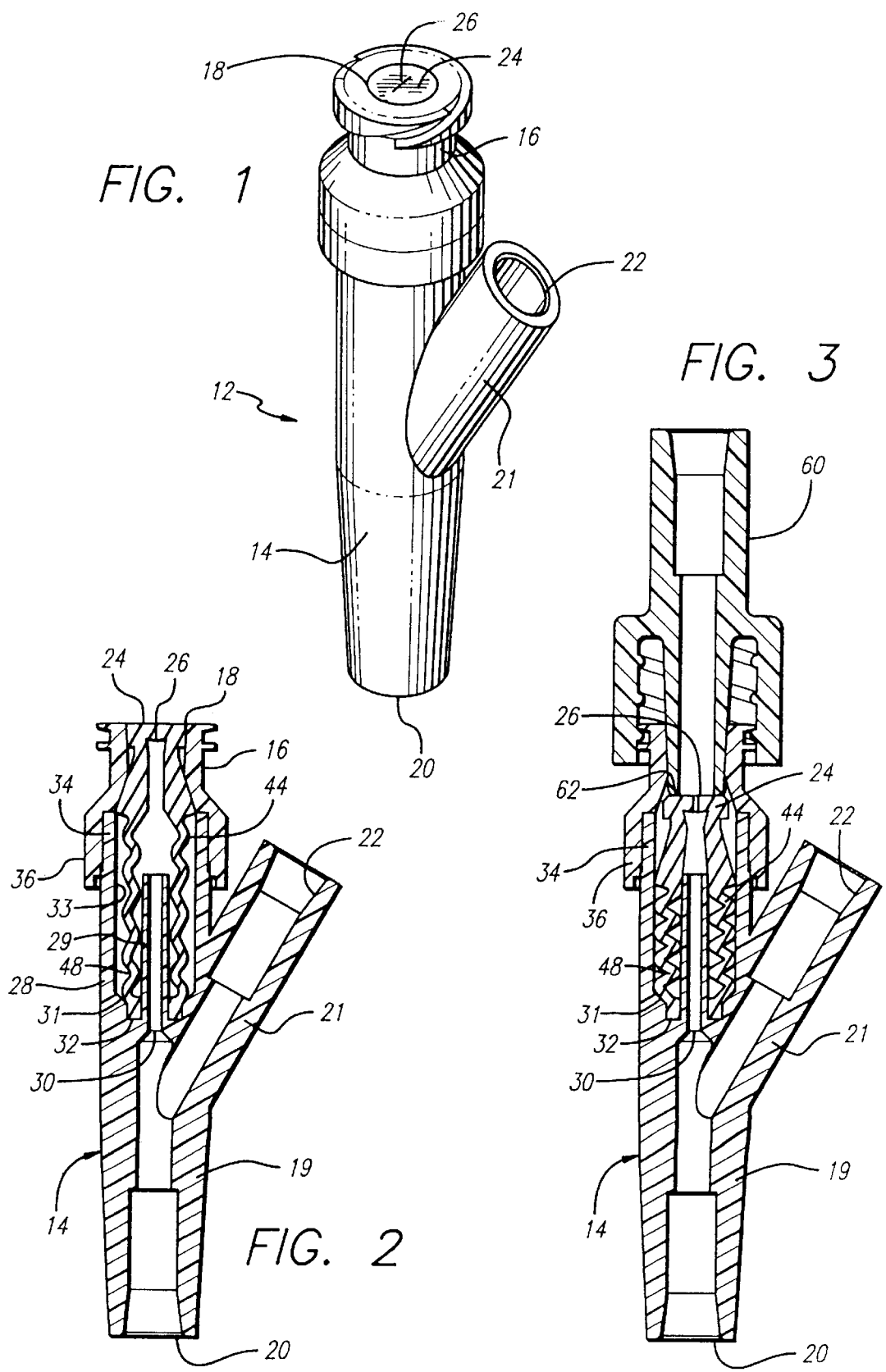

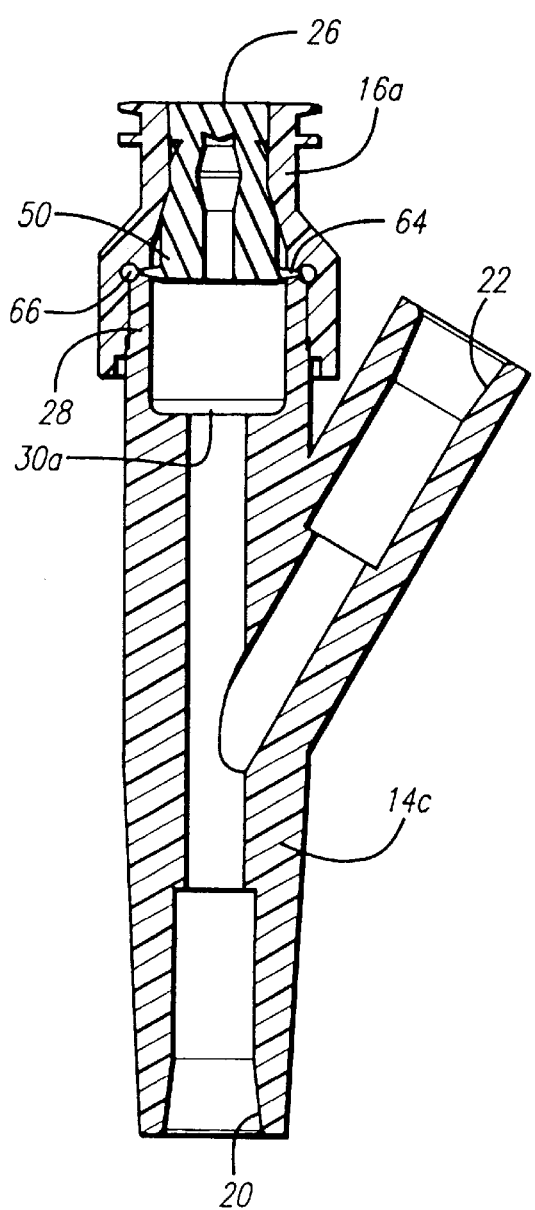
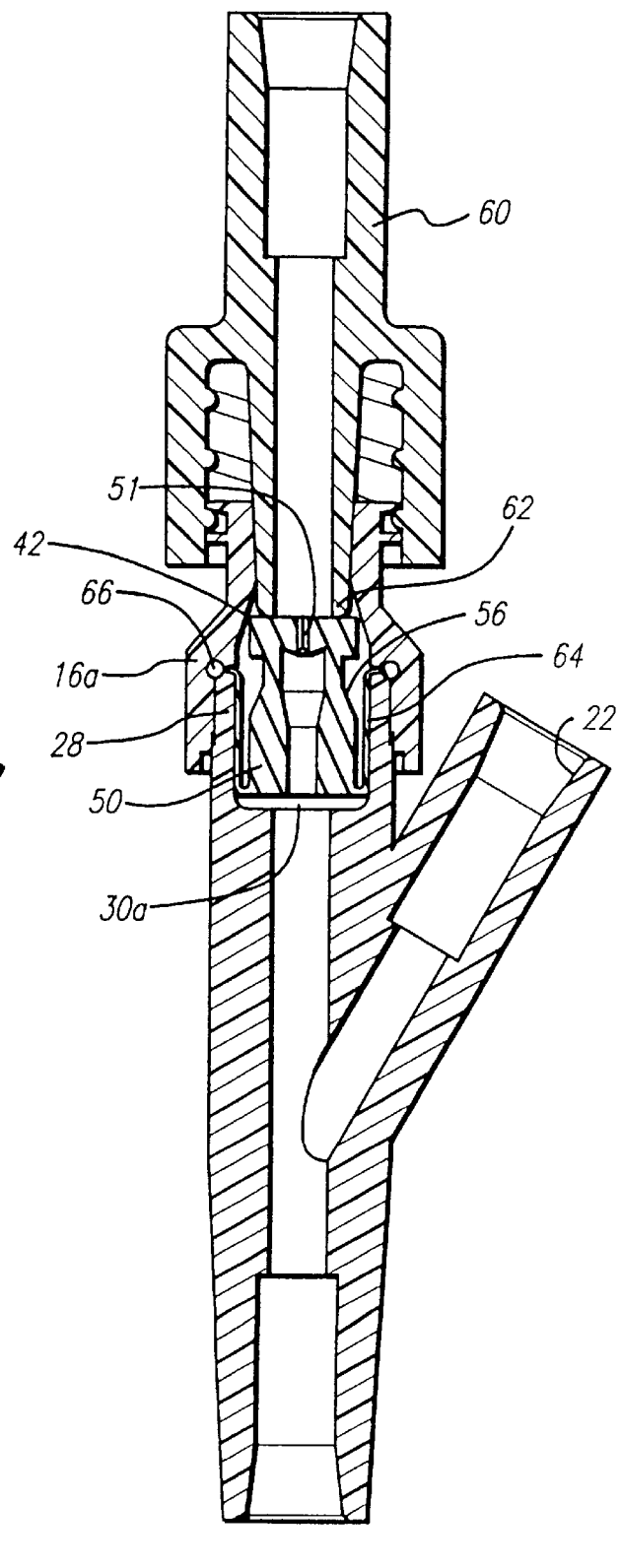

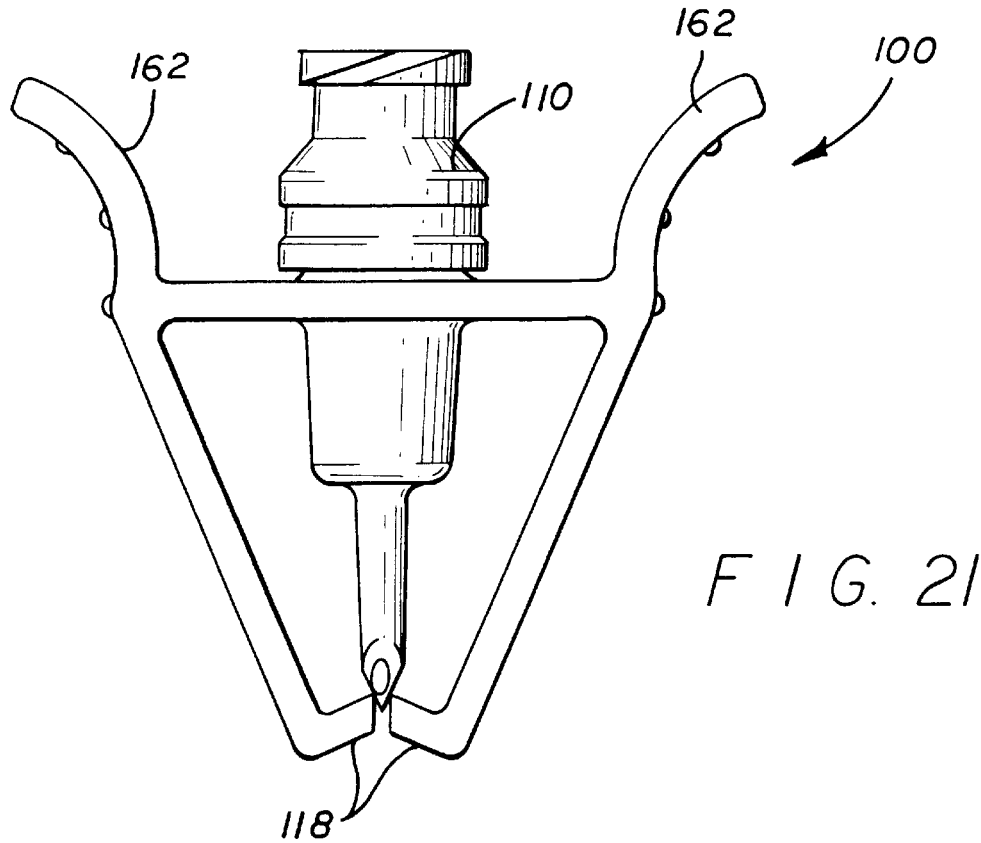
F I G. 21
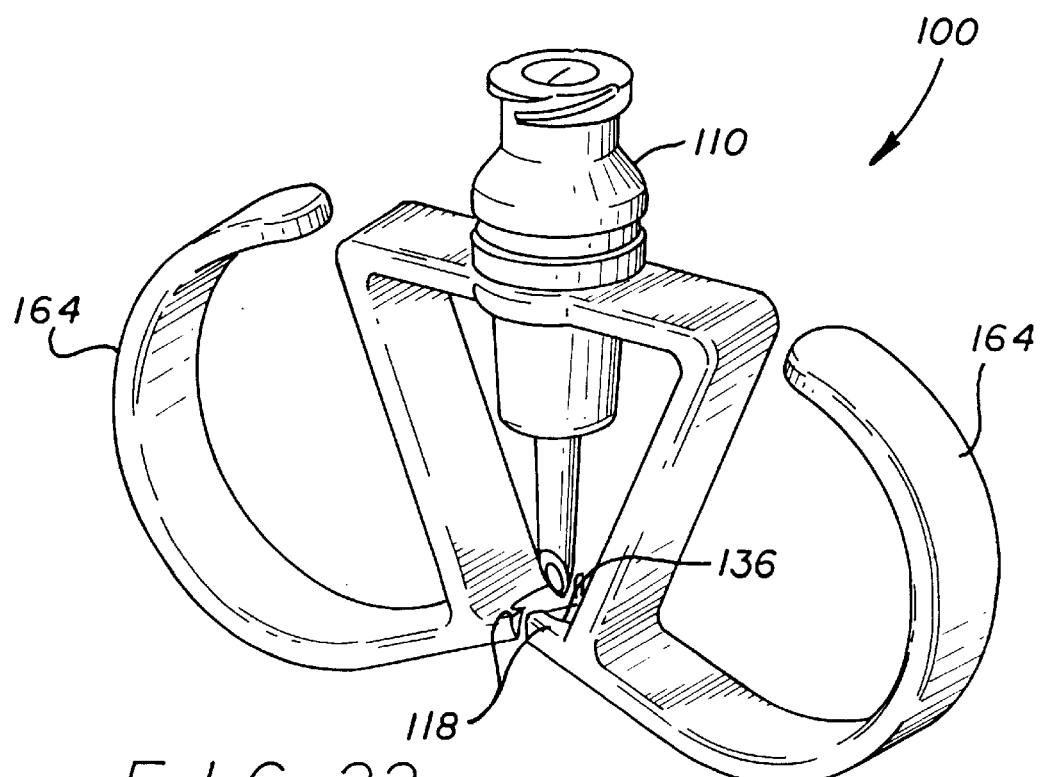
F I G. 22

6,142,446

MEDICAL ADAPTER HAVING NEEDLELESS VALVE AND SHARPENED CANNULA

This is a continuation of application Ser. No. 08/794,404 filed Feb. 2, 1997, now U.S. Pat. No. 5,839,715, which is a continuation-in-part of application Ser. No. 08/705,062, filed Aug. 29, 1996, now U.S. Pat. No. 5,676,346, which is a continuation of Ser. No. 08/442,025, filed on May 16, 1995, abandoned.

BACKGROUND

The invention relates generally to connectors of the type used in the handling and administration of parenteral fluids, and more particularly, to an adapter having both a valve mechanism for enabling a fluid interconnection to be made therewith without the use of a sharp cannula, and a sharpened cannula for interconnecting with other devices for fluid communication.

Injection sites for injecting fluid into or removing fluid from a system, such as a solution bag, a Y-site, blood tube, fluid bottle, or drug vial, are well known and widely used. Conventional injection sites generally involve a pierceable septum formed of an elastomeric material such as latex rubber or the like, captured in an access port. A sharp cannula is inserted into the access port piercing the septum to position the distal, open end of the cannula past the septum to make fluid connection with the interior of the access port. Upon withdrawal of the sharp cannula, the elastomeric septum reseals itself thus maintaining a sterile environment within the housing of the injection site. The outer surface of the septum of the injection site is wiped with an antiseptic before each use to prevent septic agents from being drawn into the access port by the piercing movement of the needle.

Due to the large number of devices available today that have pierceable septa, there is a continuing need to provide connectors that will access these devices. However, there is a large concern over the use of sharpened cannula devices. This is due, at least in part, to concern regarding the possibility of the transmission of blood-borne diseases through accidental needle punctures of persons handling the sharp cannulas. Connectors having no sharpened surfaces are desirable because such hazard is eliminated. Consequently, more recently, connectors for accommodating the injection and withdrawal of fluids without the use of sharp cannulas have been put to use in increasing numbers.

However, some existing needleless connectors suffer from various shortcomings. For example, relatively complex configurations employing a large number of parts are difficult to manufacture and assemble. This not only increases costs but may pose problems in service. Additionally, complex systems may not be intuitive to use which may prove distracting and therefore undesirable in the typical hospital room environment.

A further concern in the design of needleless connectors is the order of events in which the connection is made. For example, allowing fluid to escape or air to enter during interconnection due to the female connector being opened before the male connector is sufficiently seated is undesirable.

Additionally, some existing connectors accommodate a relatively large interior fluid volume requiring the injection of a commensurately large volume of fluid just to fill and prime the connector. If not taken into account, this fluid volume can detract from the volume of medicament injected into the patient and may be clinically significant. An inconvenient separate flushing procedure may be required in low dose injections or in the injection of unstable medicines due to this relatively large interior volume. Moreover, relatively complex geometries and the use of springs and the like in the wetted portion of the connector interior may give rise to "dead spaces" where fluid tends to linger due to poor flushing. Dead spaces give rise to problems similar to those occasioned by large interior volumes, again resulting in the inconvenient requirement of flushing.

Where metal components, such as metallic springs, are used in connectors, the metal components can interfere with magnetic resonance imaging used in hospitals. A further difficulty with the use of coiled metallic springs is the care that must be taken during manufacture. Allowing coiled springs to come into contact with each other while awaiting assembly into the valves may result in the springs becoming entangled with each other necessitating further handling before they can be installed.

Furthermore, it is desirable that needleless connectors be configured so that they can be easily cleaned by an antiseptic wipe, or otherwise sterilized, prior to making a connection. All exterior surfaces that may be involved in the transmission of fluid should be readily available for cleaning prior to the connection being made. Some prior connectors have a small rift or fissure defined by a clearance between parts. Such a feature is difficult and inconvenient to clean in attempting to sterilize a connector. Alternatively, connectors requiring cap to maintain a sterile connection port prior to use are undesirable because the extra steps involved in removing and replacing a cap are inconvenient, while the manufacture of the cap adds expense.

The ability to accommodate a high fluid flow rate is also desirable in a needleless connector. Physicians in certain situations order the administration of medicaments at high-flow rates. Some prior connectors have restrictive geometries that limit their flow capacity such that administering fluids at high rates is impossible. The use of tortuous flow paths through a connector or multiple openings through a movable valve device through which the fluid must flow can result in a reduction of the maximum rated flow rate for the connector. With some restrictive geometries, higher flow rate requirements may not be possible under gravity head flow conditions and a positive pressure pump may be needed. Such connectors would be undesirable where pumps are not available and the usefulness of such connectors would be severely limited. The increase of flow rate capability and elimination of the tortuous fluid path can also facilitate priming of the connector and reduce potential blood hemolysis.

In addition, the performance of connectors incorporated into IV administration sets and used to allow automatic piggyback administration of medicaments becomes degraded when high flow rates through the connector cannot be accommodated. If high flow rates through the connector cannot be accommodated, automatic piggyback rates using infusion pumps must be limited to relatively low infusion rates. Otherwise, accidental simultaneous flow of primary fluids may occur when normal head height differentials are used between the primary and piggyback containers. Higher flow rates through the needleless connector allows higher flow rates of automatic piggyback administration without the possibility of accidental simultaneous flow of primary fluids.

A further consideration in the design of a connector is its compatibility with other connectors. In those cases where a cannula is mounted internally in a needleless connector to slide inside the fluid port of a male connector inserted into the needleless connector to establish the flow path, the outer diameter of that cannula must be closely controlled so that it can successfully mate with a wide range of male connectors. Making it too large may result in interference with certain male connectors thus rendering them unusable with the needleless connector. However, making the outer diameter of the cannula too small results in reduced fluid flow rates through the cannula.

Additionally, the internal cannula in the connector can damage the valve itself. In particular, the cannula can pierce, cut, or tear a rubber piston or septum mounted over it and damage the resealability of the valve. The cannula could also create particulate by tearing off portions of the rubber piston or septum when a male Luer is inserted into the connector. This may occur where the bore of the male Luer interferes with or is closely sized with the cannula and creates a punching action that removes a piece of the rubber septum. Consequently, it is desirable to avoid such configurations.

To accommodate both the need for continued use of pierceable septa devices and the use of blunt or needleless connectors for increased safety, there is a need for a connector that can mate with both devices. Such a connector would "adapt" the pierceable device to a needleless or blunt cannula access system. Once in place through the pierceable septum, it is desirable for the adapter to be anchored in position so that inadvertent disengagement does not occur, such as is possible when such a connector is engaged with a fluid bag suspended upside down.

A further consideration is expense. Because connectors are used in a medical environment, cleanliness is of large concern. Contamination among different fluid devices, patients, etc. must be avoided. Typically, most connectors are disposable so that after one use, they are then discarded to avoid such contamination. Of course, expense is a major concern for disposable items. Connectors should be made of fewer parts so that the parts and manufacturing expense is kept as low as possible to lessen the expense to the patient.

A further consideration is the expense to the hospital or other care-giving facility caused by having to stock numerous types of connectors. A single connector/adapter that fits all other devices would be preferable. Typically, a hospital must stock a variety of connectors to be assured of mating with various medical fluid devices. For example, a blood tube has a different opening than a solution bag and two different connectors must be stocked.

In some cases, a connector having a sharpened spike at one end and a female Luer lock fitting at the other end must be stocked. In order to adapt this connector to a needleless connection, a needleless valve must be connected with the Luer fitting, thus requiring the hospital to stock two components. In many cases, the sharpened spike is housed within a shroud to protect the handler from inadvertently puncturing himself or herself. The shroud is unlikely to fit all components to which a connector is needed, thus requiring the hospital to stock multiple types of sharpened spike connectors. The requirement to stock various components increases expense for the hospital. It would be desirable to stock a single connector that would mate with all medical fluid devices.

Hence, those concerned with the development of medical connectors have recognized the need for an adapter usable with both a pierceable injection site and a needleless connection system. In addition, there is a need for such a connector to have a small number of parts so that expense is reduced. Further, there is a need for an adapter that can mate with a wide variety of medical fluid devices so that only a single adapter is needed, thus obviating the need to stock multiple connector components. There is also a recognized need for an improved needleless connector that has a relatively simple construction with a small number of parts, that avoids the entry of air when the initial connection is made, that has reduced flushing requirements, that can be easily cleaned prior to use, and that permits a relatively high fluid flow rate. The present invention fulfills such needs and others.

SUMMARY OF THE INVENTION

Briefly, and in general terms, the invention is directed to a medical adapter for interconnecting a pierceable site with a male fluid connector, comprising a body having a first and a second end, a needleless site located at the first end of the body, having a fluid flow port, a sharpened cannula located at the second end of the body, the cannula having a sharpened tip, an internal fluid channel interconnecting the fluid flow port of the needleless site with the sharpened cannula so that fluid may flow between the two, a first clip arm mounted to the body, the first clip arm extending to the tip of the sharpened cannula and having a distal end, and a claw at the distal end of the first clip arm facing in the direction of the sharpened cannula and protecting the sharpened tip. In another aspect, the adapter further comprises a spring connected to the first clip arm to urge the distal end of the first clip arm toward the sharpened tip of the cannula. In a more detailed aspect, the spring comprises a resilient connecting link attached between the first clip arm and the body. In a further aspect, the claw comprises a sharpened point facing the sharpened cannula.

In further aspects, the adapter comprises a second clip arm mounted to the body opposite the first arm, the second clip arm extending to the tip of the sharpened cannula and having a distal end with a claw at the distal end of the second clip arm facing in the direction of the sharpened cannula protecting the sharpened cannula. Each claw comprises a sharpened surface and two points facing the sharpened cannula. Each claw also comprises a notch facing in the direction of the sharpened cannula.

Additionally, the adapter further comprises a handle mounted to each clip arm such that applying force to the handle will cause the claw of the clip arm to move away from the sharpened cannula tip. In another aspect, the handle is located so that applying pressure to the handle in a direction toward the adapter body will cause the claw to move away from the sharpened cannula tip. In a different aspect, the handle is located so that applying pressure to the handle in a direction away from the adapter body will cause the claw to move away from the sharpened cannula tip.

In additional aspects, the lengths of the clip arms and the claws and the angle of the claws to the respective clip arms are selected so that the claws protect the sharpened tip of the cannula to prevent the sharpened tip from piercing an operator of the adapter unless the arms and claws are moved away from the sharpened tip. The lengths of the sharpened cannula and the clip arms are selected also so that the adapter will connect with various fluid devices of different sizes. The sharpened cannula length is selected to be longer than the thickest membrane to be pierced. The arms are mounted far enough away from the body of the adapter so they will not interfere with the sharpened cannula mating with devices of different sizes.

In a more detailed aspect, the body of the adapter comprises a sealing portion that has a size selected to closely fit with injection site tubing of a device to form a fluid-tight seal when engaged with the device.

In yet a further aspect, an adapter is provided having a protected, sharpened cannula at one end and a female connector at the other end for adapting a pierceable site to a male fluid connector while providing protection for the sharpened cannula to avoid punctures of an operator of the adapter. A plurality of protective shrouds are disposed about the sharpened cannula, with at least one shroud having a length equal to or greater than the sharpened cannula. The plurality of shrouds are concentric with the axis of the sharpened cannula and have different diameters. One shroud has a diameter selected to closely receive an elastomeric membrane of a device, such as the injection site of a solution bag, for a fluid-tight seal.

These and other features and advantages of the present invention will become apparent from the following detailed description of preferred embodiments which, taken in conjunction with the accompanying drawings, illustrate by way of example the principles of the invention.

BRIEF DESCRIPTION OF THE DRAWINGS

FIG. 1 is a perspective view of a connector incorporating principles of the present invention;

FIG. 2 is an enlarged cross-sectional view of the connector shown in FIG. 1 in its closed position;

FIG. 3 is an enlarged cross-sectional view of the connector shown in FIG. 2 with a male connector inserted in the connector's connection port thereby moving the piston of the connector to its open position;

FIG. 11b presents the view of FIG. 11a taken along lines 11b—11b;

FIG. 12 is an enlarged cross-sectional view of another alternative embodiment of a connector in accordance with aspects of the invention;

FIG. 13 is an enlarged cross-sectional view of the connector shown in FIG. 12 with a male connector inserted for fluid communication

FIG. 21 is the adapter of FIG. 14 with an alternate handle arrangement;

FIG. 22 is also the adapter of FIG. 14 with yet another alternate handle arrangement;

DETAILED DESCRIPTION OF PREFERRED EMBODIMENTS

Figure 6:
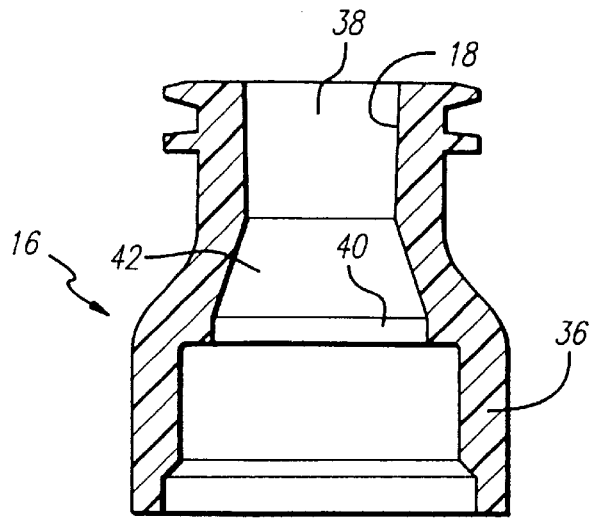
FIG. 6 is a further enlarged cross-sectional view of the Luer adapter component of the connector shown in FIGS. 1 through 5.

Referring now to the drawings in which like numerals refer to like or corresponding elements among the several figures, there is illustrated in FIGS. 1 through 3 a Y-connector incorporating a needleless valve embodying the principles of the present invention. This particular connector configuration was selected for illustration purposes only as the subject needleless valve can be embodied in any of a variety of connectors including, but not limited to, J-loops, T-Connectors, Tri-connectors, PRN adapters, Luer-locks, slip Luers, tubing engagement devices, access pins, and others.

As is shown in FIG. 1, the Y-connector 12 comprises a housing 14 terminating in an exit port 20 and having a Y-branch 21 with a Y-branch port 22. This particular embodiment also comprises a Luer adapter 16 forming a part of the housing and that adapter includes a connection port 18. The adapter is configured to receive all ANSI standard male Luer fittings, as well as other blunt cannulas or fluid conduit devices. In its unaccessed state or closed position, a piston head 24 located internally to the housing is flush with the surrounding connection port 18 and has a tightly closed orifice 26 at its center.

FIG. 2 shows in enlarged cross-section the Y-connector of FIG. 1 with the needleless valve in its closed position. The Y-branch 21 leads to the Y-branch port 22 and the distal section 19 of the housing 14 extends between the Y-branch and the exit port 20. The housing 14 includes a tubular section 28 having a circular cross-section, an exit orifice 30 at its base 31, a support tube 29 extending upwardly from the base, and a groove 32 formed in the base surrounding the support tube. The exterior surface of the tubular section 28 near its proximal end is stepped slightly inwardly 34 to receive the Luer adapter 16 thereover and provide ultrasonic weld geometry. Alternatively, the adapter and the housing may be joined by a spin weld, snap fit, by bonding, or by other means.

Figure 5:
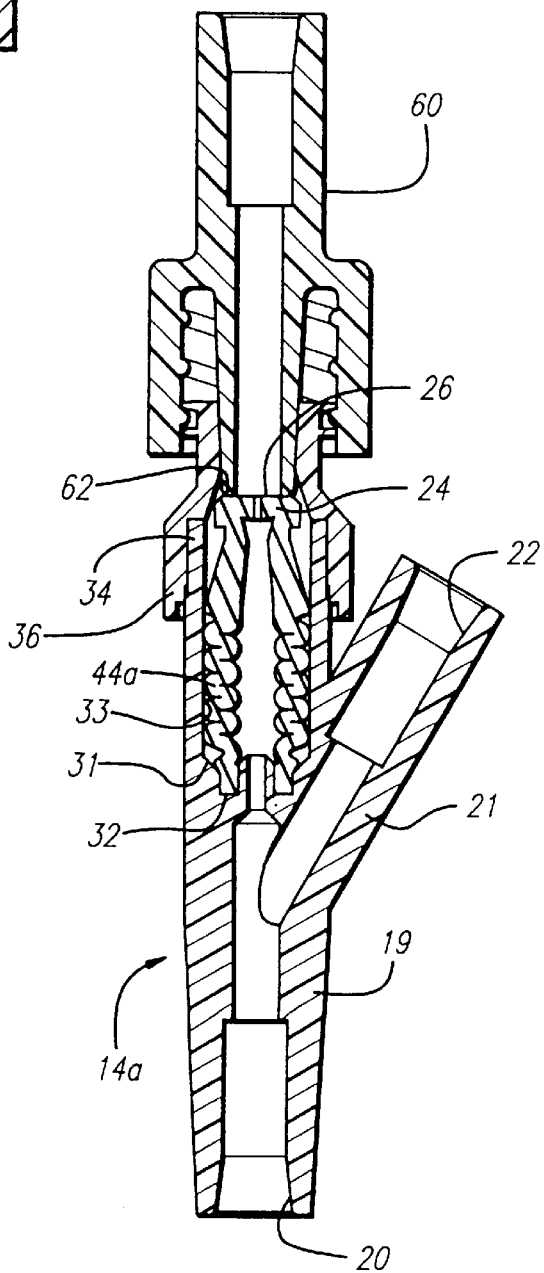
FIG. 5 is a cross-sectional view of the connector shown in FIG. 4 with a male connector inserted in the connector's connection port thereby moving the piston of the connector to its open position.
Figure 4:
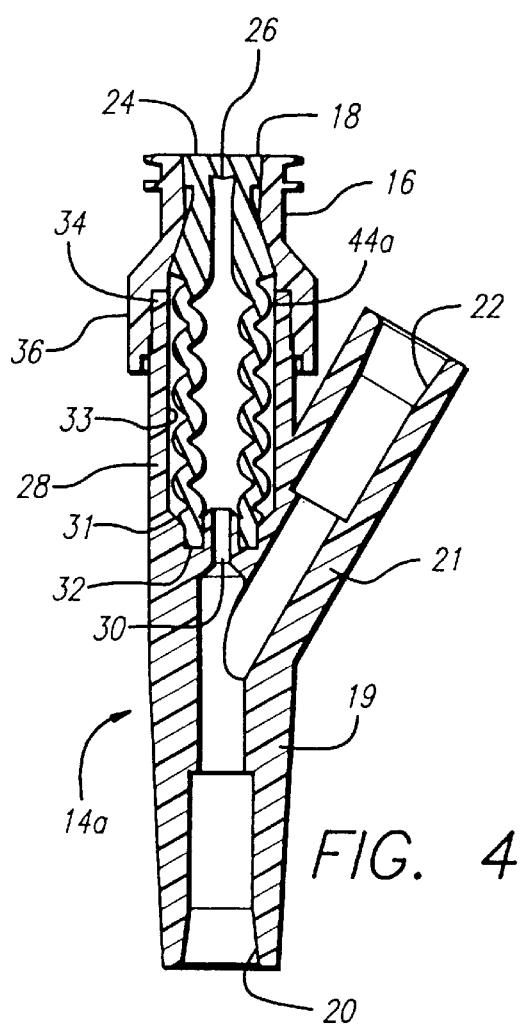
FIG. 4 is a cross-sectional view of an alternative embodiment of a connector incorporating principles of the invention and showing it in its closed position.

FIG. 2 additionally shows the piston element 44 in place within the bore 33 of the tubular section 28 captured between the Luer adapter 16 and the base 31. The piston element 44 includes a total of four bellows. The alternative embodiment illustrated in FIGS. 4 and 5 is similar to the embodiment shown in FIGS. 2 and 3, with the exception that the support tube 29 has been deleted, and the piston element 44a has a total of five bellows of shallower angle.

As is illustrated in FIG. 6, the interior of the Luer adapter 16 has sections of various diameters. The section directly adjacent the connection port 18 comprises a standard ANSI Luer taper section 38 that incorporates a very slight inward taper. The center section 40 has a substantially larger diameter and is separated from the taper section 38 by the tapered ramp/lock section 42. Additionally, the inner diameter of the center section 40 is slightly larger than the inner diameter of the tubular section 28 of the body 14 for reasons discussed below. Finally, the Luer adapter 16 includes a skirt 36 that is dimensioned to fit over the stepped proximal end 34 of the tubular section 28 to provide ultrasonic weld geometry. The adapter 16 may be molded of a material containing a phosphorescent colorant to render the connector visible in a darkened room.

As is generally shown in FIGS. 2 through 5, a resiliently deformable piston element 44 and 44a is captured between the base 31 of the tubular section 28 and the Luer adapter 16 in the bore 33 of the housing 14. While the details of its structure vary slightly from embodiment to embodiment, the views of element 44a shown in FIGS. 7a and 7b serve to illustrate many of the common features. The piston element's structure 44a which is molded in its entirety of rubber in this embodiment generally includes a piston 46 and a compressible section 48. The piston 46, in turn, includes a piston head 24 that is elliptical in cross-section and a thick taper-lock portion 50 that is circular in cross-section. A marquise-shaped bore 51 is formed along the longitudinal axis of the piston head 24 and terminates in an orifice 26 at its proximal end and a taper lip seal 59 at its distal end. The taper lip seal 59 comprises a pair of lips 54 that extend from opposed sides of the bore's sides. The lips comprise conical sections that extend from the bore's sides to function as a seal.

Figures 7A, 7B:
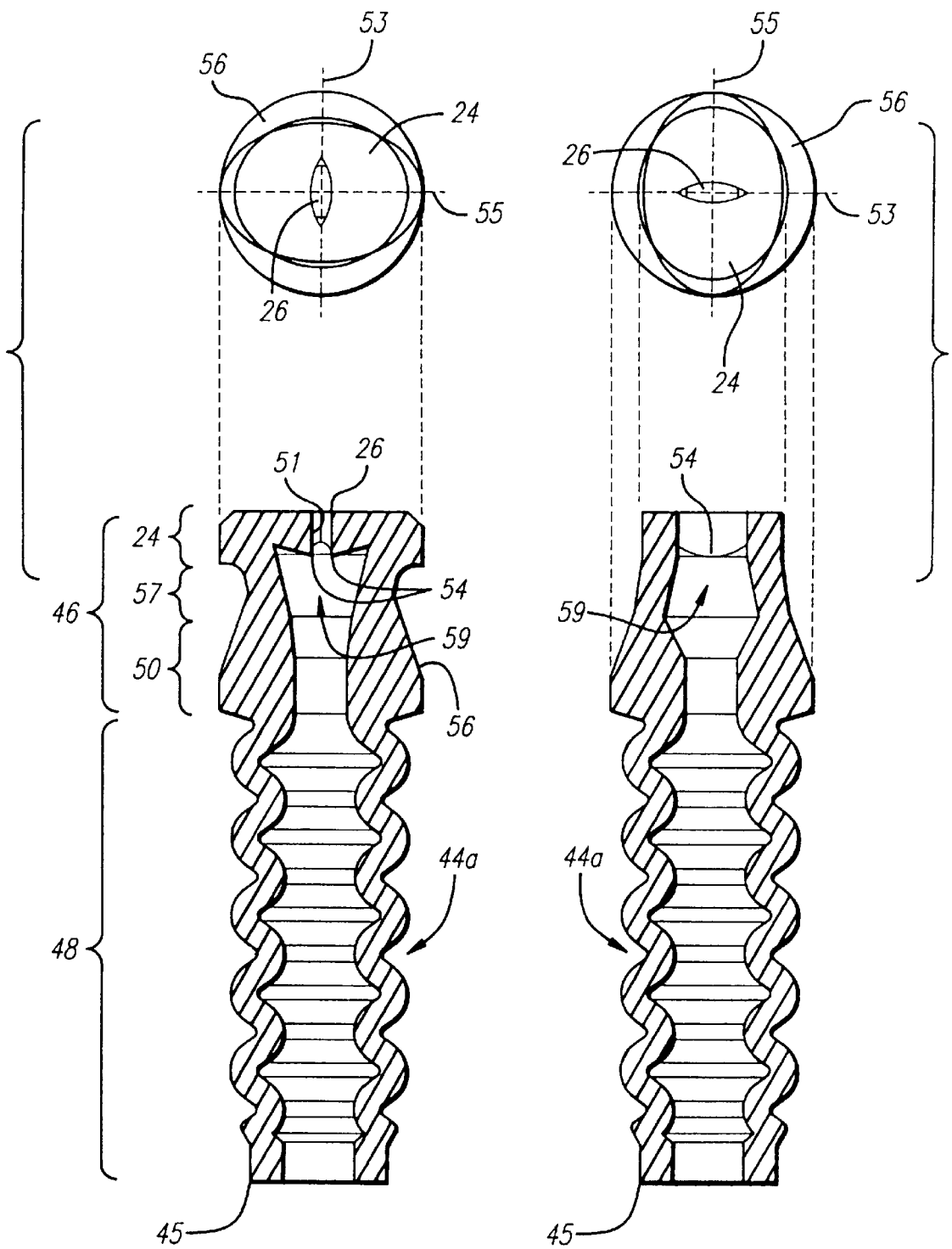
FIGS. 7a and 7b are further enlarged cross-sectional side and top views of the piston component of the connector shown in FIG. 2 with the views rotated 90° from each other.

As is apparent when comparing FIGS. 7a and 7b, the marquise-shaped bore 51 is oriented such that its major axis 53 is perpendicular to the major axis 55 of the elliptically-shaped piston head. Additionally, the transitional section 57 between the piston head 24 and the taper lock portion 50 is elliptical and conical in shape wherein the major axis of such ellipse is parallel to the major axis 55 of the piston head and perpendicular to the major axis 53 of the bore 51. This geometry further assists in naturally biasing the marquise-shaped bore into its open position. This elliptical shape creates an outward force parallel to the major axis of the elliptical shaped piston head and an inward force parallel to that same axis. The inward force tends to compress the piston in a direction perpendicular to its major axis and thus tends to pull the marquise-shaped bore open when a male Luer applies force to the top of the piston moving the piston into the center section 40 of the adapter 16.

The taper-lock portion 50 of the piston element 44 is fairly thick in order to prevent it from being compressed. This thicker section helps to hold the piston in the valve at higher internal pressures and also acts as a divider between the spring action below and the opening and closing of the marquise-shaped bore above. Although the piston element 44 is seated in the base 31 of the housing tightly, extreme internal pressures may provide a substantial force to push the piston element 44 out of the housing 14 thereby destroying its integrity. This thickened portion 50 of the piston element provides added assurance that it will not compress under such internal forces and will hold the piston in position in the housing.

Figure 8A:
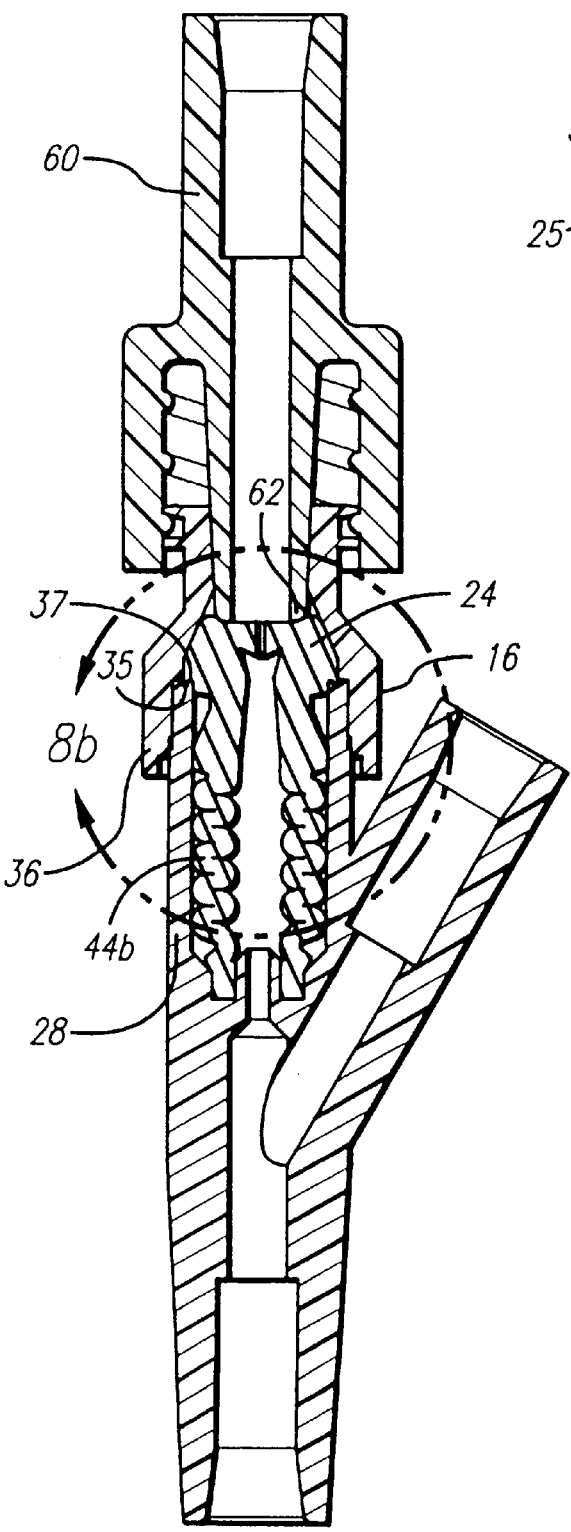
FIG. 8a is a cross-sectional view of an alternative embodiment of a connector incorporating principles of the invention.
Figure 8B:
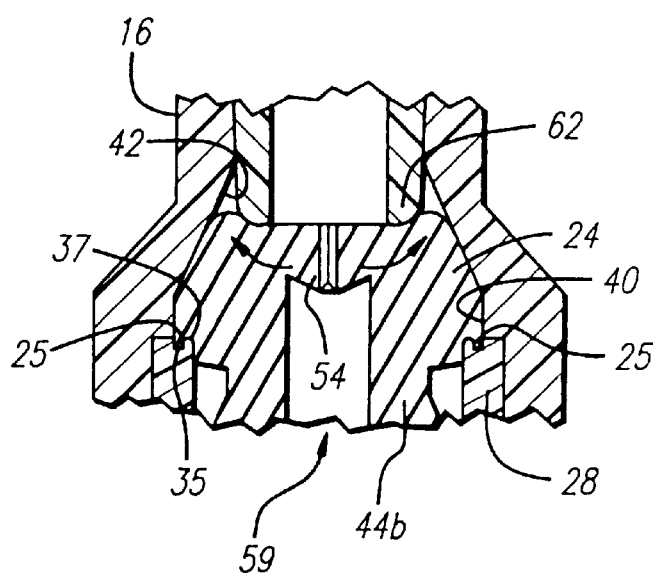
FIG. 8b is a further enlarged cross-sectional view of a portion of the connector of FIG. 8a showing the piston with an inserted male connector.

FIGS. 8a and 8b illustrate an alternative embodiment wherein the inner diameter of the tubular section 28 is sufficiently reduced relative the inner diameter of the center section 40 of the adapter 16 to accommodate an annular groove 35 formed in its proximal edge. Sections of a circular groove 37 are formed on each end of the major axis 55 of the bottom of the elliptical piston head 24 to provide hooks 25. The hooks are configured so as to engage the groove 35 in the tubular section. Once the hooks have engaged the groove as a result of the male Luer 62 pushing the piston 24 farther into the adapter 16, the hooks will oppose further movement of the periphery of the piston and will result in any further male Luer forces causing the bore 51 to open wider, as shown in FIG. 8b.

Figure 9:
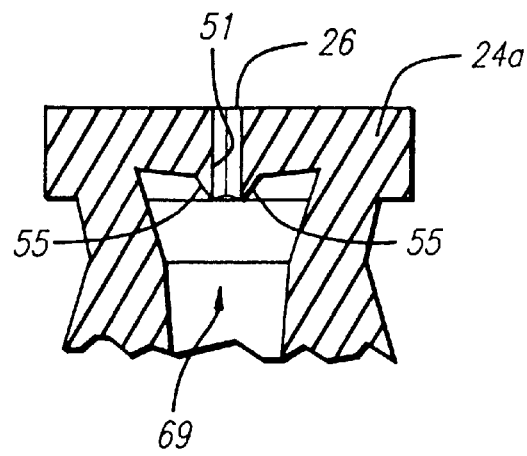
FIG. 9 is a greatly enlarged cross-sectional view of an alternative embodiment piston head.

FIG. 9 illustrates an alternative embodiment wherein a pair of flexible flaps 55 extend from about the bore 51 to provide a check valve 69. This opposes the back flow of fluid while the piston element is in its closed state.

Returning now to FIGS. 7a and 7b, the bore 51, in conjunction with the hollow interior of the taper lock section 50 and the hollow interior of the compressible section 48, forms a fluid path through the entire piston element 44. The compressible section 48 may comprise an accordioned configuration as shown in FIGS. 2–5, 7a, 7b, and 8a or, alternatively, an annularly or helically ribbed structure that similarly allows for the controlled collapse of the structure along its longitudinal axis to generate a restoring force. Some alternative embodiments are illustrated in FIGS. 10a through 10d and show possible variations in the number, size, and configuration of the ribs or bellows. Different shapes of the piston element may be used to improve flow rate, activation force, spring return rate, sealing, piston retention, and acceptance of blunt cannulas. The piston geometry variations could also improve the valve function with fluids that easily solidify by removing internal annular grooves and pinch point areas. Modifications include changing the number of bellows, ribs, wall thickness, height, diameter, durometer, color, and geometry. Pinch point areas are formed from the accordioned folds that come together upon compression of the piston and could, under certain conditions, trap solidified fluids to interfere with the compression of the piston.

Figure 10A:
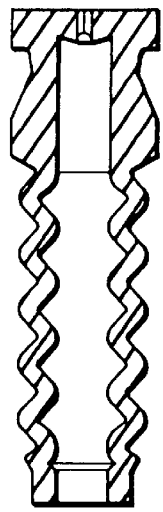
FIGS. 10a through 10d present different configurations of a piston element usable in a connector of the present invention.
Figure 10B:
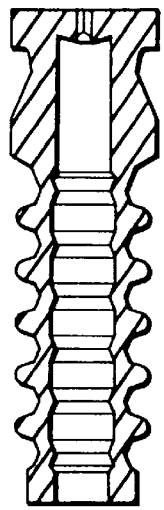
Figure 10C:
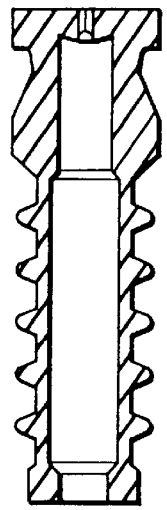
Figure 10D:
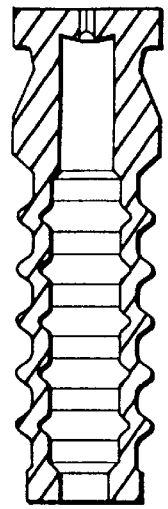

In particular, FIG. 10a shows a compressible section having five bellows as per FIGS. 4, 5, 7, and 8 which require a reduced activation force. FIG. 10b shows a compressible section having an external ribbed structure wherein the compressed shape has no pinch points. FIG. 10c shows the compressible section of the piston element with straight walls to increase activation force and reduce pinch points. FIG. 10d shows a compressible section which provides a smooth interior surface upon compression to increase the flow rate.

Returning again to FIGS. 2,3, 7a, and 7b, the distal end 45 of the compressible section 48 is received in the groove 32 in the base 31 of the tubular section 28 to form a tight seal about the support tube 29 and the exit orifice 30. The piston element is lubricated with FDA approved silicone oil to facilitate movement of the piston within the connector and to prevent the bore 51 through the piston head 24 from being sealed closed during sterilization.

Figure 11A:
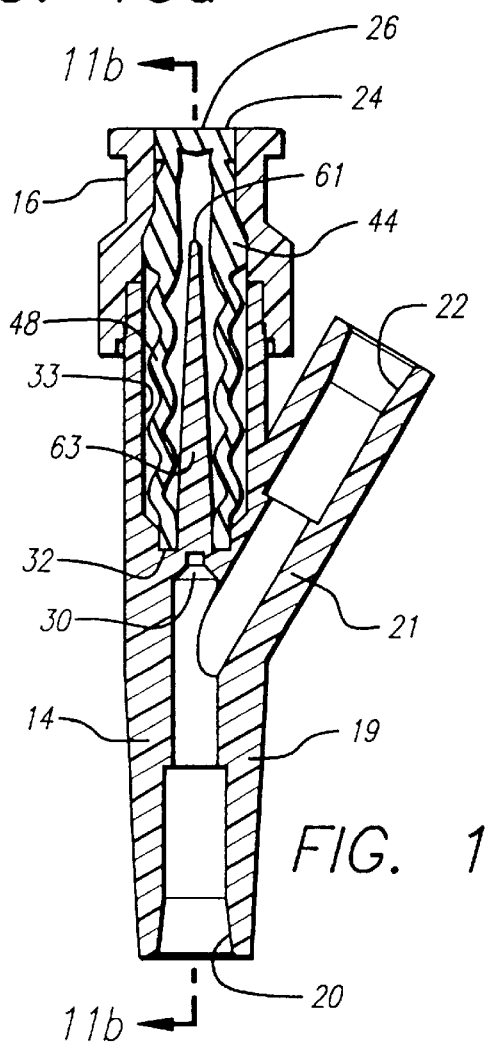
FIGS. 11a and 11b illustrate cross-sectional views of an alternative embodiment of a connector incorporating principles of the present invention in which a center post is included.
Figure 11B:
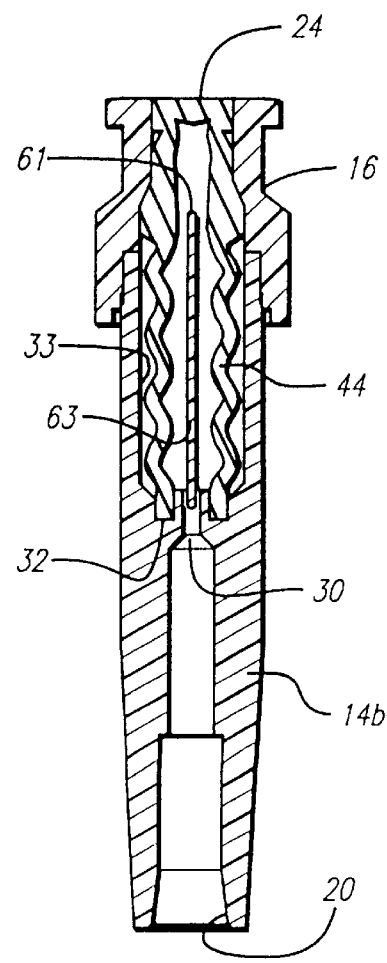

In the alternate embodiments illustrated in FIGS. 11a and 11b a support structure, in the form of a flattened post 63, has been added to the interior of the tubular section 28 so as to project into the compressible section 48 of the piston 46. The post has a rounded tip 61 that extends into the bore 51 of the piston element 24 upon depression of the piston 44 to assist in its opening. Clearance between the post's tip 61 and the pointed ends of the marquise-shaped bore 51 facilitates flow thereby, while clearance between the thinner dimension of the flattened post 63 and the interior surface of the collapsible section 48 allows for the flow of fluid into the exit orifice 30.

FIGS. 12 and 13 illustrate a further alternative embodiment wherein an extension spring in the form of a diaphragm 64 serves to bias the piston 46 into its closed position, rather than the compression spring approach shown in the other figures. The diaphragm 64 extends from the base of the taper lock section 50 and has an annular bead 66 formed about its periphery. Such bead is captured between the Luer adapter 16 and the proximal edge of the tubular section 28. Grooves are formed in these respective elements to ensure a positive grasp of the bead element 66. The position of the bead 66 relative its point of attachment to the taper lock section 50, and the sizing of the diaphragm 64 ensure that the diaphragm is pre-loaded such that it biases the tapered shoulder 56 of the piston 46 into contact with the taper lock section 42 of the adapter 16.

Turning now to a more detailed discussion of the operation of the valve shown in the various figures, the dimensions of the elliptical piston head 24 and the marquise-shaped bore 51 are selected such that when the head is constrained into the circular interior of the ANSI Luer taper section 38 of the Luer adapter 16, the bore is completely collapsed to tightly close off the orifice 26 and cause the adjacent lips 54 of the taper lip seal 59 to abut one another. The tapered shoulder 56 of the taper lock section 50 contacts the ramp/lock section 42 of the adapter 16 and prevents the top of the piston head 24 from extending beyond the connection port 18. The internal diameter of the center section 40 of the Luer adapter 16 is selected such that the piston head 24 is free to assume its elliptical shape when positioned therein. This, in turn, allows the bore 51 to reassume its natural marquise-shape thereby opening a fluid path through the piston and the connector.

Referring now to the embodiments shown in FIGS. 2–11, the needleless connector is initially in its unaccessed state or closed position as shown in FIG. 2, 4, 11a, and 11b. The compressible section 48 is pre-loaded and causes the piston head 24 to be biased into the ANSI Luer taper section 38 (FIG. 6) of the Luer adapter 16. The shoulder 56 of the taper-lock section 50 contacts the tapered ramp/lock section 42 of the adapter 16 and prevents the top of the piston head 24 from extending beyond the connection orifice 18 to form a smooth and flush surface. The bore 51 throughout the piston head 24 is tightly squeezed shut by virtue of the normally elliptically shaped piston head being constrained into the circular cross-section of the ANSI Luer taper section 38. The sharp pointed ends of the marquise-shaped bore facilitate a tight seal upon compression of the bore along its minor axis by compression of the piston head 24 along its major axis. The taper lips 54 of the taper lip seal 59 or, alternatively, the flexible flaps 55 of the check valve 69 further ensure that the bore 51 remains sealed even when subjected to substantial internal pressures. The diaphragm element 64 employed in the alternative embodiment shown in FIGS. 12 and 13 similarly serves to bias the piston head 24 into the ANSI Luer taper section of adapter 16.

Just prior to accessing the connector, the piston head 24 and the edge of the connection port 18 are cleaned by, for example, passing a sterilizing swipe over the smooth surface. The absence of ridges, grooves, gaps, or protrusions ensure that proper cleanliness is achieved. The connector is then ready to be accessed by a standard male Luer with or without a Luer lock.

As the male Luer tip 62 of the male Luer connector 60 (FIGS. 3, 5, 8, and 13) is brought into contact with the top surface of the rubber piston head 24, a seal is formed to preclude the passage of liquidator air there between. The application of sufficient pressure causes the compressible section 48 of the piston element 44 to compress or, alternatively, diaphragm 64 to stretch, and the piston head 24 to be moved out of the ANSI Luer taper section 38 and into the center section 40 (FIG. 6). As the piston head clears the tapered ramp/stop section 42 and is moved into the center section 40, its larger internal diameter allows the piston head to assume its naturally elliptical open shape. This, in turn, allows the bore 51 to assume its natural marquise-shape thereby opening a fluid path through the piston head. Continued pressure by the male Luer causes the piston head to be advanced into the tubular section 28 of the main body 14.

In FIGS. 8a and 8b, the slightly reduced inner diameter of the tubular section 28 relative to the diameter of the center section 40 of the adapter 16 serves to further enlarge the orifice 26 of the bore 51 by forcing rubber material up around the outside of the male tip 60. The hooks 25 formed in the bottom edge of the taper lock section 50 engage an annular groove 35 to positively pull the bore 51 open. The center section 40 of the Luer adapter 16 may be formed to have an elliptical shape wherein its minor axis is sized slightly smaller than the minor axis of the piston head 24. This serves to compress the piston head along its minor axis further ensuring that the bore attains its fully opened shape. In the alternative embodiment shown in FIGS. 11a and 11b, slight penetration of the rounded tip 61 of the post 63 into the bore 51 positively ensures the opening of the bore. The fact that the tip is rounded and of relatively small diameter prevents it from damaging the piston. It has been found that the embodiment of the post 63 shown does not cut, tear, or cause a punching action on the piston when the piston is moved into contact with the post 63.

In this position, the connector is fully accessed to provide a short, straight, unobstructed fluid path through the connector. At no time does fluid flow about the outside of the piston element on its way through the connector. A "residual" volume, i.e., the volume between the male Luer and the exit orifice, of as little as 0.04 ml is attainable. Air leakage, or the entry of contamination, as well as the escape of fluid from the device, is precluded at all times.

In the embodiment shown in FIGS. 2 and 3 and the alternative embodiment shown in FIGS. 11a, 11b, the support tube 29, and the center post 63, respectively, serve to prevent the compressible section 48 from buckling and closing off the fluid path. The flattened cross-sectional shape of the post 63 ensures adequate clearance adjacent the compressed accordioned section 48 to provide for flow at all times. In the embodiment shown in FIG. 3, fluid is directed through the center of the support tube 29.

As the male Luer is withdrawn, the biasing force generated by the compressible section 48 of the piston element 44, or the stretchable diaphragm 64 of the alternative embodiment shown in FIGS. 12 and 13, maintains contact between the piston head 24 and the male Luer tip 62. The slightly larger diameter of the center section 40 of the Luer adapter 16 (FIG. 6) relative to the tubular section 28 causes the piston taper-lock section 50 to freely move into position with the shoulder 56 (FIG. 7a) abutting the ramp/lock section 42 (FIG. 6). Simultaneously, the elliptical piston head 24 is guided into the ANSI Luer taper section 38 by the tapered ramp/lock section 42 where it is once again forced into the constrained circular shape of the ANSI Luer taper section to close off the bore 51 and reestablish a positive seal. A similar operation occurs with the embodiment shown in FIGS. 12 and 13.

Figures 14, 16:
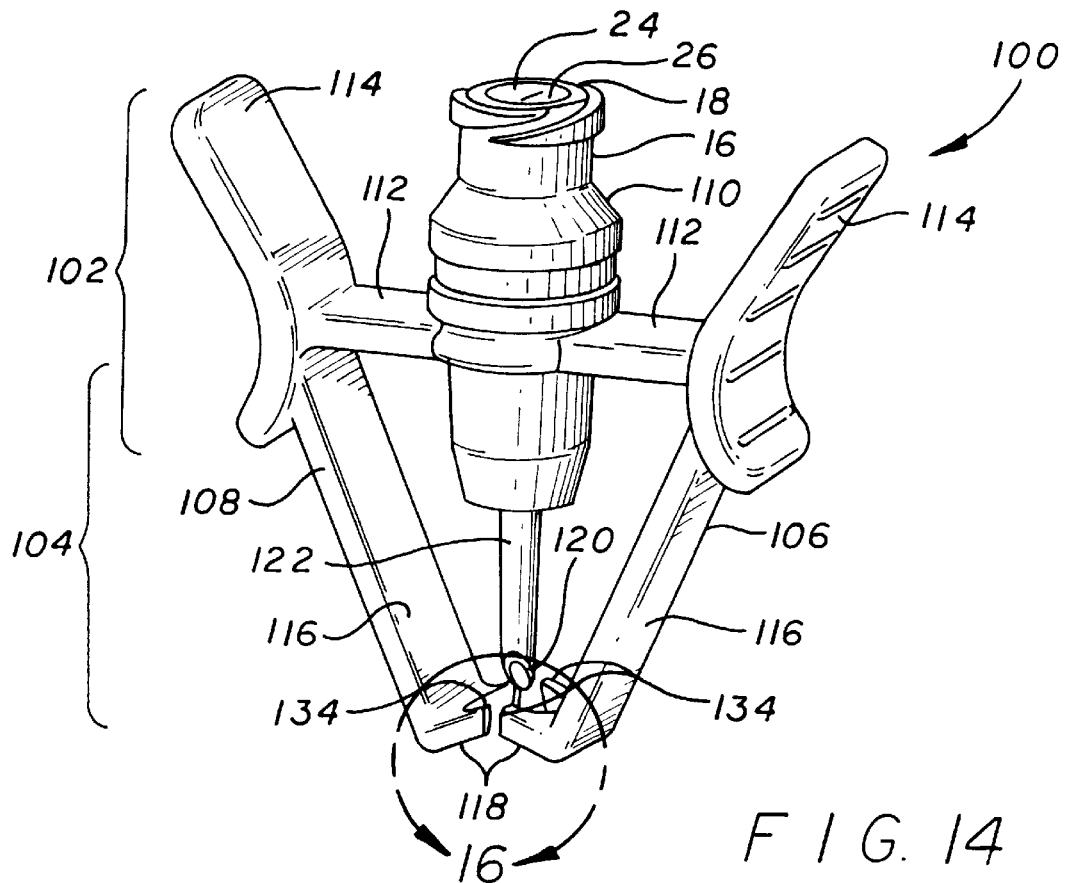
FIG. 14 is a perspective view of a medical adapter having a needleless valve access port and a sharpened cannula in accordance with aspects of the invention.
FIG. 16 is a detailed view of the claws of the medical adapter of FIG. 14 along lines 16.

Referring now to FIG. 14, there is shown a medical adapter 100 having a needleless valve section 102 and a sharpened cannula section 104. Also included are two spring clips 106 and 108 on opposite sides of a generally tubular-shaped body member 110. Each spring clip 106 and 108 includes a spring 112, a handle 114, an arm 116, and a claw section 118. At rest, as shown in FIG. 14, the springs 112 are approximately perpendicular to the body 110 and the claws 118 are almost touching. In other embodiments, the springs may be mounted such that they have different angles in relation to the body. The arms 116 and the claws 118 are configured so that when the adapter 100 is not installed through a pierceable membrane for fluid flow, the arms and claws cover the sharpened point 120 of the cannula 122 to reduce the likelihood of inadvertent punctures when handling.

The needleless valve section 102 of the adapter 100 includes the piston head 24 containing an opening 26 (also shown in FIG. 20), as shown and described previously.

Figure 15:
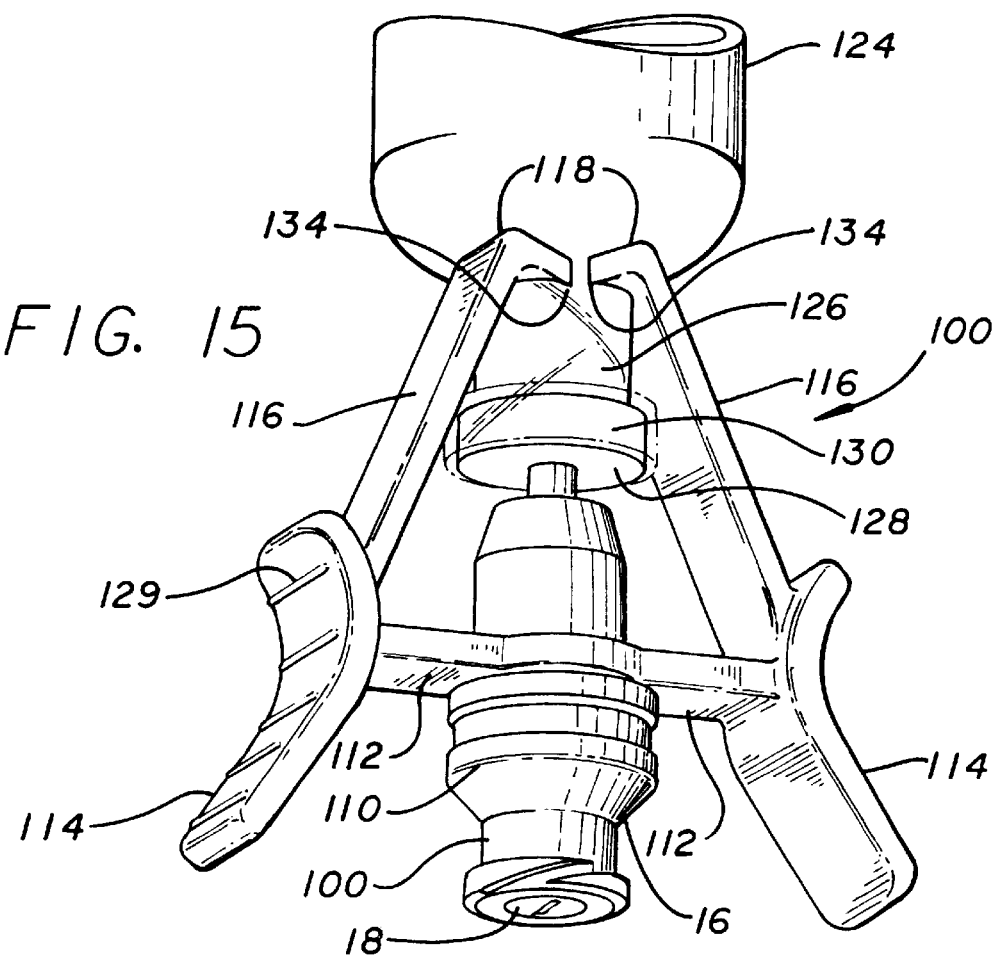
FIG. 15 is a view of the medical adapter of FIG. 14 showing the sharpened access cannula piercing the rubber septum of a drug vial.

Shown in FIG. 15 is an application of the adapter of FIG. 14 to a drug vial 124. The arms 116 of the adapter are located on either side of the neck 126 of the bottle and the spike 122 has pierced the elastomeric septum 128. In spreading apart the arms, the operator would press inward on both handles 114 until the claws 118 clear the flange 130 of the bottle opening, and then pierce the septum 128 with the spike, as shown. The handles include raised ridges 129 in this embodiment, to assist the operator in pressing the handles inward. Because pressing the handles 114 inward causes the springs 112 to bend, they will tend to straighten themselves thereby urging the claws 118 toward each other and maintaining the claws 118 in contact with the bottle neck 126. The claws will therefore not be able to be pulled past the flange 130 of the vial thereby preventing the spike from disengaging from the septum 128 of the bottle. Additionally, the friction of the spike in the septum 128 tends to keep the adapter 100 in place. A needleless connector, such as a male Luer taper fitting, may be inserted into the needleless connection port 18 to open the valve created by the piston 44 (not shown) and permit fluid flow. Fluid may be conducted into the vial 124, for mixing purposes for example, and may be conducted out of the vial, into a patient for example. The needleless connector port in FIG. 15 also has a male Luer lock fitting.

Figure 17:
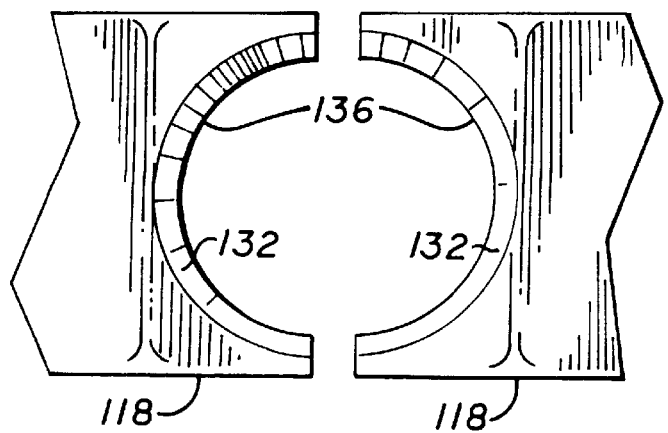
FIG. 17 is a detailed end view of the claws from a different angle along lines 17—17 of FIG. 16.

Referring now to FIGS. 16 and 17, detail of the claws 118 can be observed. The claws are located at an angle to the arms 116 which in this case is 90°. Other angles may be used. A bevel 132 is formed on each claw to result in a sharp interior edge and two points 134 (also seen in FIG. 14). Additionally, as is more apparent in FIG. 17, a circular notch 136 is formed in each claw. Because the radius of the notch would be correct for only one neck size, its primary purpose is to result in the two sharp points 134 on each claw 118 for engaging a variety of devices to hold the connector in place. Secondarily however, the notch may provide a fit with a rounded device of the proper size for even greater surface contact between the claw and the device.

Figure 18:
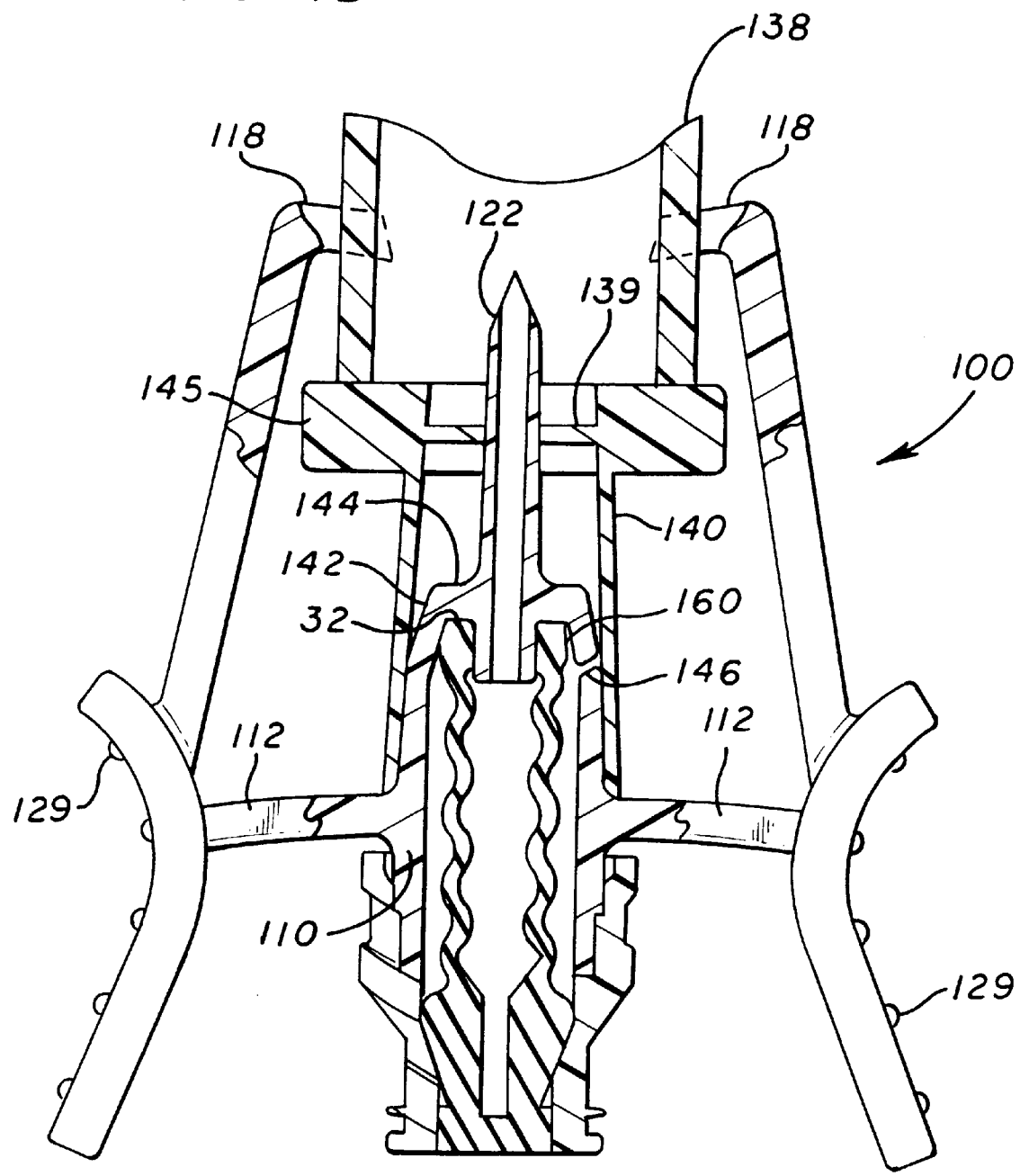
FIG. 18 is a partial cross-section view of the medical adapter of FIG. 14 showing the sharpened access cannula piercing the plastic membrane of a solution bag and forming a fluid seal with the injection port tubing of the bag.

Turning now to FIG. 18 which shows a cross section of certain elements, the adapter 100 has been engaged with the injection port of a fluid bag. The injection site of the fluid bag comprises a thin plastic membrane 139 that the sharpened cannula 122 has penetrated for fluid communication with the interior of the bag and any contents therein. The claws 118 have engaged the tubing 138 of the bag due to the action of the springs 112. The fluid bag includes a sealing tubing 140 forming a part of the opening of the bag. The sealing tubing 140 has been engaged by the adapter 100 in a fluid-tight relationship. The body 110 of the adapter includes a taper 142 between the base 144 of the sharpened cannula 122, which has a larger radius than the cannula, and the sealing portion 146 of the body 110. The sealing portion 146 has a size selected to provide a tight fit between it and the inner diameter of the sealing tubing 140 of the bag for a fluid-tight seal. Any fluids dripping from the pierced membrane 139 of the bag will not pass the seal created by the sealing portion 146 and the tubing 140. Thus the adapter 100 can be left in position in the sealing tubing 140 for later use. The taper 142 on the body 110 assists in guiding the sharpened cannula 122 and the sealing portion 146 into the sealing tubing 140 of the bag for easier engagement. Typically, a twisting motion is used to insert the body 110 fully into the sealing tubing 140 to establish a fluid-tight seal.

Figure 19:
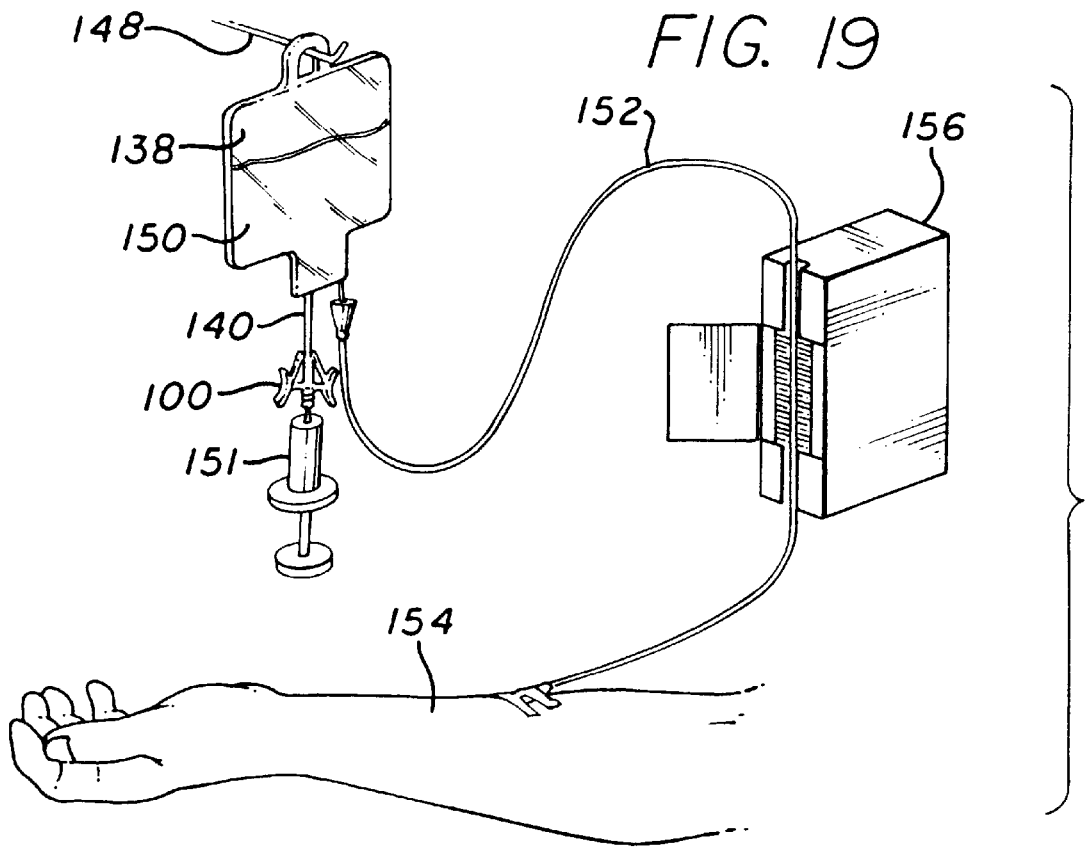
FIG. 19 is a view of an application of the adapter of FIG. 14 with a fluid solution bag and a syringe, showing also a fluid administration set used with an infusion pump and a patient.

FIG. 19 presents an application of the adapter 100 shown in FIG. 18. The solution bag 138 is inverted and hung from a hangar 148. The adapter 100 has been inserted and has pierced the thin membrane of the bag as shown in FIG. 18 thus establishing fluid communications with the medical fluid 150 in the bag. A syringe 151 has been inserted into the needleless valve section 102 of the adapter 100 for drawing fluid 150 from the bag or inserting fluid into the bag. The other port of the bag 138 is connected to a fluid administration set 152 that includes a sharpened cannula (not shown) piercing the bag port, tubing, and a cannula applied to a patient 154. To control the administration of the medical fluid 150 to the patient 154, a volumetric infusion pump 156 operates on the tubing in a process well known to those skilled in the art to accurately meter the fluid 150 to the patient. Although not clearly shown, the infusion pump in this case comprises peristaltic fingers and a pressure plate (not shown) to accurately control the flow of medical fluids through the tubing 152 to the patient.

Because the neck of the bag, which the claws 118 engage, is formed of a resilient plastic material, the sharp edge 134 of the claws achieve a grip on the bag. Additionally, there is a substantial amount of friction between the sealing portion 146 and the tubing 140 so that it is unlikely that the adapter 100 will fall out of the bag 138 due to the weight of the syringe 151, even if full. Additionally, the configuration of the claws at an angle to the arms further resists disengagement with the bag because before the adapter 100 could drop off the bag, the claws would likely hit the flange 145 of the bag formed by the membrane 139. The spring force will typically be large enough to prohibit the arms from moving outward on their own or in response to the weight of the syringe.

The length of the springs and the length of the arms are selected so as to successfully engage any device to which the adapter may be used. Because the springs and arms are relatively long, they will successfully engage small as well as large devices. In select applications, the length of each may be reduced, as desired.

It should therefore be appreciated that the adapter 100 adapts the pierceable bag membrane to a needleless connection. The adapter 100 may be left in place while the bag is connected, disconnected, and reconnected to fluid administration sets 152 as required. The adapter 100 is fluid tight with the sealing tubing of the bag and contains an internal and fully integrated needleless valve 102 so that unless a connector is engaged with the adapter 100, no fluid will flow.

Figure 20:
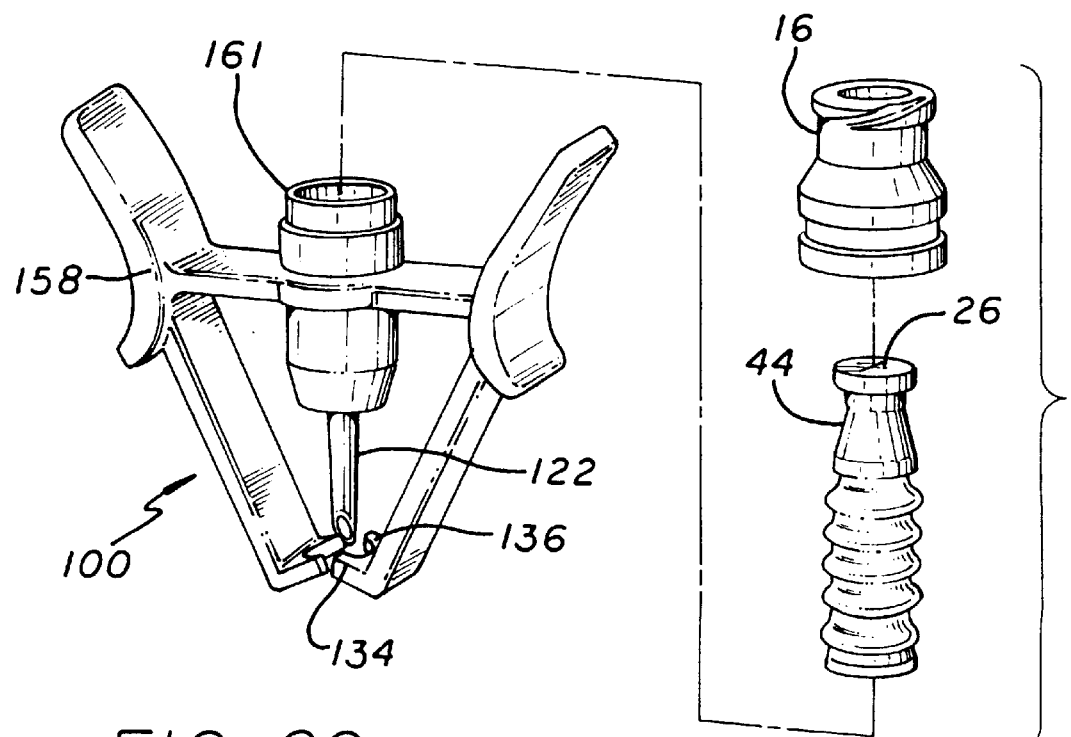
FIG. 20 is an exploded view of the medical adapter of FIG. 14.

FIG. 20 presents an exploded view of the adapter 100 of FIG. 14. In this embodiment, the adapter comprises only three parts: a Luer adapter 16; a piston 44; and the sharpened cannula section 158. The sharpened cannula section 158 is constructed as one piece and includes the springs, handles, arms, claws, sealing portion, taper, and sharpened cannula. The piston 44 is friction fit into the sharpened cannula section 158 as can be seen more clearly in FIG. 18. The groove 32 is formed to have a tight fit with the piston 44 to retain the piston. For ease in assembly, a vent 160 is formed in the side wall of the sharpened cannula section 158 to allow air to escape during assembly of the tight fitting piston in the groove 32. The proximal end 161 of the sharpened cannula section is ultrasonically welded to the Luer adapter 16 for final assembly of the adapter 100. This small number of parts and ease in assembly results in reduced cost for the adapter 100. In other embodiments, a larger number of parts may be used to construct the adapter. For example, the sharpened cannula 122 may be a separate part attached to the base 144. It may be formed of a metallic substance.

Referring now to FIGS. 21 and 22, two alternate handle designs are shown. In FIG. 21, the handle 162 comprises only a curved segment on the needleless valve section side of the springs. The operator would press the handles 162 inward toward the body 110 to open the claws 118. In FIG. 22, each handle 164 comprises two curved segments located on the sharpened cannula side of the springs for receipt of the operator's fingers or thumb and fingers. The operator would pull on the handles 164 to separate the claws 118.

Thus it will be appreciated that a versatile adapter has been disclosed. The design of the adapter is such that the sharpened cannula is protected from inadvertent punctures of operators yet can successfully be used to adapt pierceable septa to use with needleless devices. Both a sharpened cannula and a needleless connector are included in one adapter thus obviating the need for two separate devices. A restrictive, single-sized shroud is not used to protect the sharpened cannula. The protective arms in accordance with the invention move out of the way when inserting the sharpened cannula thus permitting the adapter to be used with a wide variety of devices. Thus the adapter also obviates the need to stock various sizes of connectors, as the adapter in accordance with the invention is capable of fitting numerous devices of varying sizes. For example, the adapter will successfully connect to solution bags, blood tubes, drug vials, Y-sites, and pre-slit and unslit injection sites. The length of the sharpened cannula is selected to be longer than the thickest rubber septum or membrane and the lengths of the arms and springs are selected to be long enough to fit over and around all of the above-listed devices. Because of the small number of components forming the adapter, the priming volume is significantly reduced and the dead space in the adapter, in which fluid will pool, is also significantly reduced or eliminated. This results in more fluid reaching the patient and less fluid being lost as overhead, or adapter lost fluid.

Alternate embodiments are possible, as is likely apparent to those skilled in the art. In one case, a barb or barbs may be added to the sharpened cannula so that the sharpened cannula cannot be removed once inserted into the septum.

Figure 23:
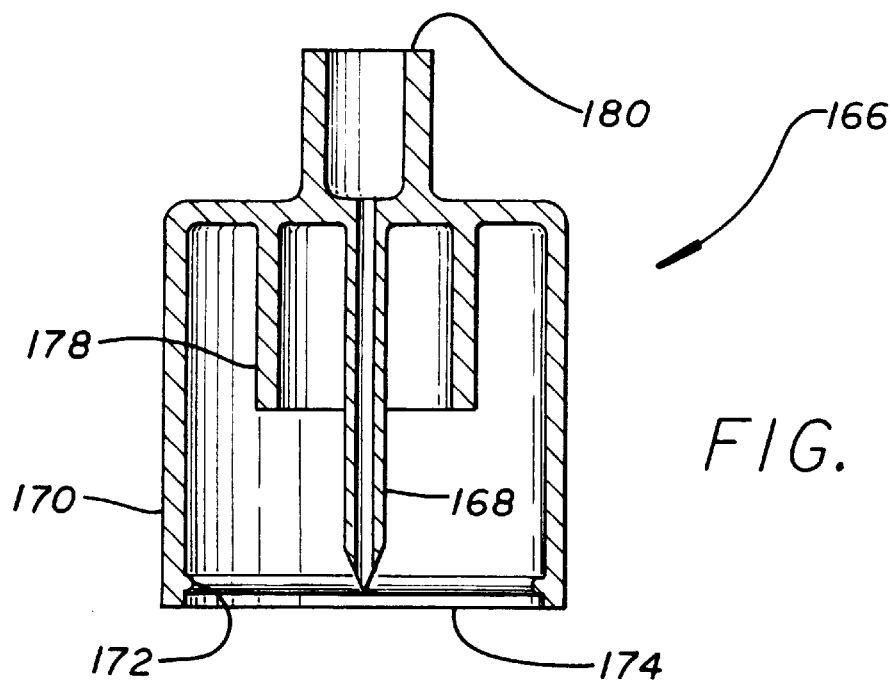
FIG. 23 is a cross-section diagram of an adapter having a sharpened cannula at one end and a female connection at the other end for receiving a male fluid connector, with a plurality of shrouds surrounding the sharpened cannula and a raised ridge to assist in holding the adapter in place.
Figure 24:
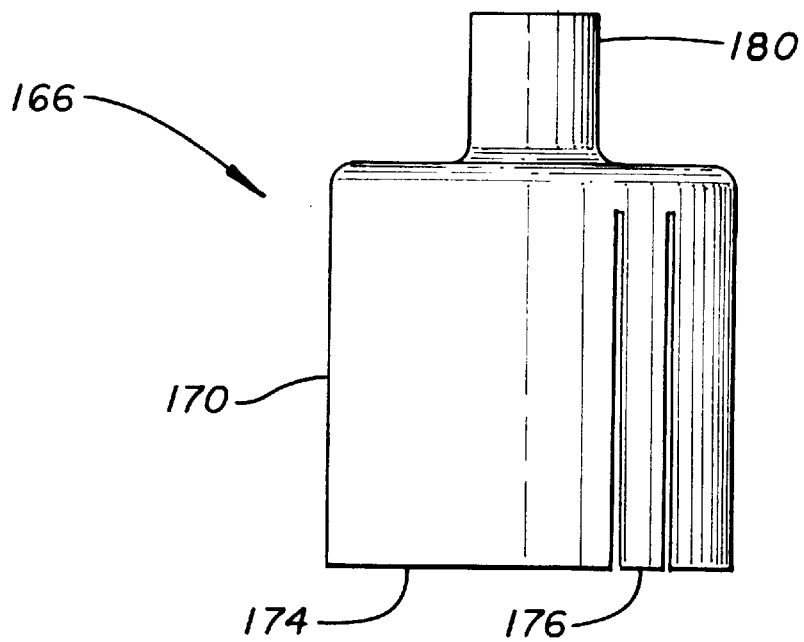
FIG. 24 is a diagram of the adapter of FIG. 23 showing a spring arm formed in a shroud for gripping a device to which the sharpened cannula would be engaged.

An alternate embodiment of a protected adapter 166 is shown in FIG. 23 and 24. In this embodiment, a sharpened cannula 168 is disposed within a plurality of protective shrouds. In this case, the outer shroud 170 is at least as long as the sharpened cannula 168 to protect the cannula from puncturing an operator of the adapter 166. A raised ridge 172 is formed near the open end 174 of the outer shroud 170. The raised ridge disposed completely around the inside surface of the outer shroud assists in retaining the adapter in place over a pierceable site. As the shroud is forced over the site, the ridge will also snap over the flange of the site, for example, and will retain the adapter 166 in place.

As an alternative to the raised ridge of FIG. 23 that continues completely around the inside surface, FIG. 24 presents an embodiment where an arm 176 has been formed in the outer shroud 170 by forming two slots in the axial direction. Although not shown, a raised ridge would be formed on the inside surface of the arm 176 to function in the same way as the ridge in FIG. 23. Because the slots forming the arm are relatively lengthy, the arm can move outward and inward in relation to the shroud 170. Its connection to the shroud acts as a spring urging the arm 176 back to its position level with the shroud 170.

Returning now to the cross-section view of FIG. 23, an inner shroud 178 is concentric with the sharpened cannula 168, as is the outer shroud, and is shorter than the outer shroud. The inner diameter of the inner shroud 178 is selected to closely fit with the elastomeric septum provided with the injection port of solution bags. Forcing the elastomeric septum into the inner shroud creates a fluid-tight seal. The sharpened cannula is long enough to pierce the plastic membrane of the injection port of a solution bag, shown in FIG. 18, as the elastomeric septum (not shown) seals with the inner shroud. The elastomeric septum has been removed from the injection port shown in FIG. 18.

In FIG. 23, a female Luer fitting 180 is formed at one end of the adapter. A needleless valve may be disposed in the adapter 166 instead of only the female Luer fitting, similar to the configuration shown in FIG. 18.

While particular forms of the invention have been illustrated and described, it will also be apparent to those skilled in the art that various modifications can be made without departing from the spirit and scope of the invention. Accordingly, it is not intended that the invention be limited except by the appended claims.

What is claimed is:

1. A valve mechanism for forming a fluid-flow path within a medical connector having a hollow housing extending between an inlet port and an exit port, the housing having a first section of a first cross-sectional shape and size near a second section of a second cross-sectional shape and size, the second cross-sectional size greater than the first cross sectional size, said valve mechanism comprising:

a resiliently deformable piston head located within the housing such that the entire piston head is movable between the first and second sections, the piston head having a bore therethrough and a cross-sectional shape different from the first cross-sectional shape, the piston head having a maximum cross-sectional size greater than the first cross-sectional size such that when the piston head is within the first section the bore is closed; and a resiliently deformable hollow biasing segment for biasing the piston head into the first section.

2. The valve mechanism of claim 1 wherein the maximum cross-sectional size is such that when the piston head is within the second section the bore is open.

3. The valve mechanism of claim 1 wherein the piston head is elliptical in cross-section and the first section of the housing is circular in cross-section.

4. The valve mechanism of claim 3 wherein the bore has a marquise-shaped cross-section having its major axis oriented perpendicularly to the major axis of the elliptical piston head.

5. A valve mechanism for forming a fluid-flow path within a medical connector having a hollow housing extending between an inlet port and an exit port, the housing having a first section of a first cross-sectional shape and size near a second section of a second cross-sectional shape and size, the second cross-sectional size greater than the first cross sectional size, said valve mechanism comprising:

a resiliently deformable piston head located within the housing such that the entire piston head is movable between the first and second sections, the piston head having a marquise-shaped bore therethrough and a cross-sectional shape different from the first cross-sectional shape, the piston head having a maximum cross-sectional size, the bore oriented such that its major axis is perpendicular to the direction of the maximum cross-section, the maximum cross-sectional size being greater than the first cross-sectional size such that when the piston head is within the first section the bore is closed; and a resiliently deformable hollow biasing segment for biasing the piston head into the first section.

6. The valve mechanism of claim 5 wherein the size of the maximum cross-section is such that when the piston head is within the second section the bore is open.

7. The valve mechanism of claim 5 wherein the piston head is elliptical in cross-section and the first section of the housing is circular in cross-section.

8. The valve mechanism of claim 7 wherein the maximum cross section comprises the major axis of the elliptical piston head.

9. A valve mechanism for forming a fluid-flow path within a medical connector having a hollow housing extending between an inlet port and an exit port, the housing having a first section of a first cross-sectional shape and size near a second section of a second cross-sectional shape and size, the second cross-sectional size greater than the first cross sectional size, said valve mechanism comprising:

a resiliently deformable piston head located within the housing such that the entire piston head is movable between the first and second sections, the piston head having a bore therethrough and a cross-sectional shape different from the first cross-sectional shape, the piston head having a maximum cross-sectional size greater than the first cross-sectional size such that when the piston head is within the first section the bore is closed;

a resiliently deformable hollow biasing segment for biasing the piston head into the first section; and a lock section at the junction of the piston head and the biasing segment, the lock section having a maximum cross-sectional size greater than the first cross-sectional size to limit proximal movement of the piston head to a position substantially flush with the inlet port.

10. A medical connector comprising:

a hollow housing including an adapter having an inlet port and a distal section having an exit port, the adapter having a first section of a first cross-sectional shape and size near a second section of a second cross-sectional shape and size, the second cross-sectional size greater than the first cross sectional size; and a valve mechanism for forming a fluid-flow path between the inlet port and the exit port, the valve mechanism comprising a resiliently deformable piston head entirely movable between the first and second sections, the piston head having a bore therethrough and a cross-sectional shape different from the first cross-sectional shape, the piston head having a maximum cross-sectional size greater than the first cross-sectional size such that when the piston head is within the first section the bore is closed, the valve mechanism further comprising a resiliently deformable hollow biasing segment for biasing the piston head into the first section.

11. The medical connector of claim 10 wherein the housing further includes a tubular section between the adapter and the distal section, the biasing segment is positioned within the tubular section, and the tubular section has an inner diameter greater than the maximum cross section of the biasing segment.

12. The medical connector of claim 11 further comprising a support tube disposed within the tubular section near the junction of the tubular section and the distal section, the support tube sized such that the biasing segment may be disposed about the support tube.

13. The medical connector of claim 11 further comprising a post disposed within the tubular section near the junction of the tubular section and the distal section, the post sized such that the biasing segment may be disposed about the support tube.

14. The medical connector of claim 13 wherein said post has a flattened cross sectional shape.

15. The medical connector of claim 13 wherein the post is sized length-wise such that upon movement of the piston head into the second section the tip of the post extends into the piston head.

16. The medical connector of claim 10 wherein the size of the maximum cross-section is such that when the piston head is within the second section the bore is open.

17. The medical connector of claim 10 wherein the piston head is elliptical in cross-section and the first section of the housing is circular in cross-section.

18. The medical connector of claim 17 wherein the bore has a marquise-shaped cross-section having its major axis oriented perpendicularly to the major axis of the elliptical cross-section of the piston head.

19. The medical connector of claim 18 wherein the second section of the housing is circular in cross-section and the diameter of the second section is greater than the diameter of the first section.

20. The medical connector of claim 10 further comprising a lock section at the junction of the piston head and the biasing segment, the lock section having a maximum cross-sectional size greater than the first cross-sectional size to limit proximal movement of the piston head to a position substantially flush with the inlet port.

* * * * *